United States Patent [19]

Whisson

[11] Patent Number: 5,624,185
[45] Date of Patent: Apr. 29, 1997

[54] DEVICE FOR MIXING AND MEASURING A QUANTITY OF LIQUID

[75] Inventor: Maxwell E. Whisson, Nedlands, Australia

[73] Assignee: Max-Medical Pty Ltd., Nedlands, Australia

[21] Appl. No.: 592,339

[22] PCT Filed: Aug. 5, 1994

[86] PCT No.: PCT/AU94/00449

§ 371 Date: Apr. 25, 1996

§ 102(e) Date: Apr. 25, 1996

[87] PCT Pub. No.: WO95/04591

PCT Pub. Date: Feb. 16, 1995

[30] Foreign Application Priority Data

Aug. 5, 1993 [AU] Australia ................................. PM0420

[51] Int. Cl.$^6$ ........................................................ B01F 11/00
[52] U.S. Cl. ................................................ 366/141; 366/208
[58] Field of Search ............................. 366/110–112, 114, 366/141, 208–211, 213, 215, 216, 219

[56] References Cited

U.S. PATENT DOCUMENTS

| 1,602,196 | 10/1926 | Iverson et al. | 366/216 X |
|---|---|---|---|
| 2,552,188 | 5/1951 | Krause et al. | |
| 2,757,375 | 7/1956 | Rieutord et al. | 366/211 |
| 3,607,478 | 9/1971 | Henninges et al. | 366/208 X |
| 3,698,494 | 10/1972 | Gaudin | 366/141 X |
| 4,026,531 | 5/1977 | Luchsinger et al. | 366/211 |
| 4,125,335 | 11/1978 | Blume et al. | |

FOREIGN PATENT DOCUMENTS

| 2544220 | 4/1983 | France . |
|---|---|---|
| 2567416 | 7/1984 | France . |
| 2574540 | 12/1984 | France . |
| 91/10503 | 7/1991 | WIPO . |

OTHER PUBLICATIONS

Derwent Abstracts Accession No. 22532C/13, Class J02, JP.A. 5020626 (Mochida Pharm. KK) 14 Feb. 1978.

*Primary Examiner*—Charles E. Cooley
*Attorney, Agent, or Firm*—Merchant, Gould, Smith, Edell, Welter & Schmidt, P.A.

[57] ABSTRACT

A mixer comprising a platform (12) which is configured to be able to support a receptacle containing a quantity of liquid. The platform (12) being supported from a base (18) to be pivotable about a first axis and a second axis where the first and second axes are perpendicular to each other, a drive motor (37, 39, 40 and 42) provided between the base (18) and the platform (12) to cause joint pivotable movement of the platform (12) about both the first and second axes to effect a rocking action of the platform (12). A particular application of the invention relates to a device which can be used during blood collection to facilitate both mixing and quantity measurement of the blood being collected.

23 Claims, 4 Drawing Sheets

DEVICE FOR MIXING AND MEASURING A QUANTITY OF LIQUID

FIELD OF THE INVENTION

This invention relates to a device which can be used to effect mixing of liquids.

SUMMARY OF THE INVENTION

A particular application of the invention relates to a device which can be utilised during blood collection to facilitate the mixing of the blood being collected with an anticoagulant in such a way that the blood components to not become segregated. It should be appreciated however, that the invention need not be limited in its scope to such an application.

Accordingly, the invention resides in a mixing means comprising a central support, a transverse member extending to each side of the central support, a platform supported from the transverse member to be pivotable about a substantially horizontal first pivot axis and about a second pivot axis which is transverse to the first pivot axis, a drive motor supported from the transverse member having an upright drive shaft which is coupled to the platform whereby rotation of the drive shaft causes joint pivotal movement of the platform about the first and second pivot axes and whereby the spacing between the drive shaft and platform is not affected by the loading on the platform, wherein the loading on the central support by the transverse member is substantially balanced, a portion of the transverse member to each side of the centeral portion being resiliently deflectable in proportion to the weight of the contents of the platform, a measuring means provided to measure the degree of deflection of the portions to provide an indication of the weight and/or volume of the contents of the platform.

According to a preferred feature of the invention said platform is configured to receive a receptacle in the form of a closed bag formed of a flexible material. Preferably the platform is formed as a tray having upstanding sides.

The invention will be more fully understood in the light of the following description of one specific embodiment. The description is made with reference to the accompanying drawings of which:

DETAILED DESCRIPTION OF THE PREFERRED EMBODIMENT

Figure 1:
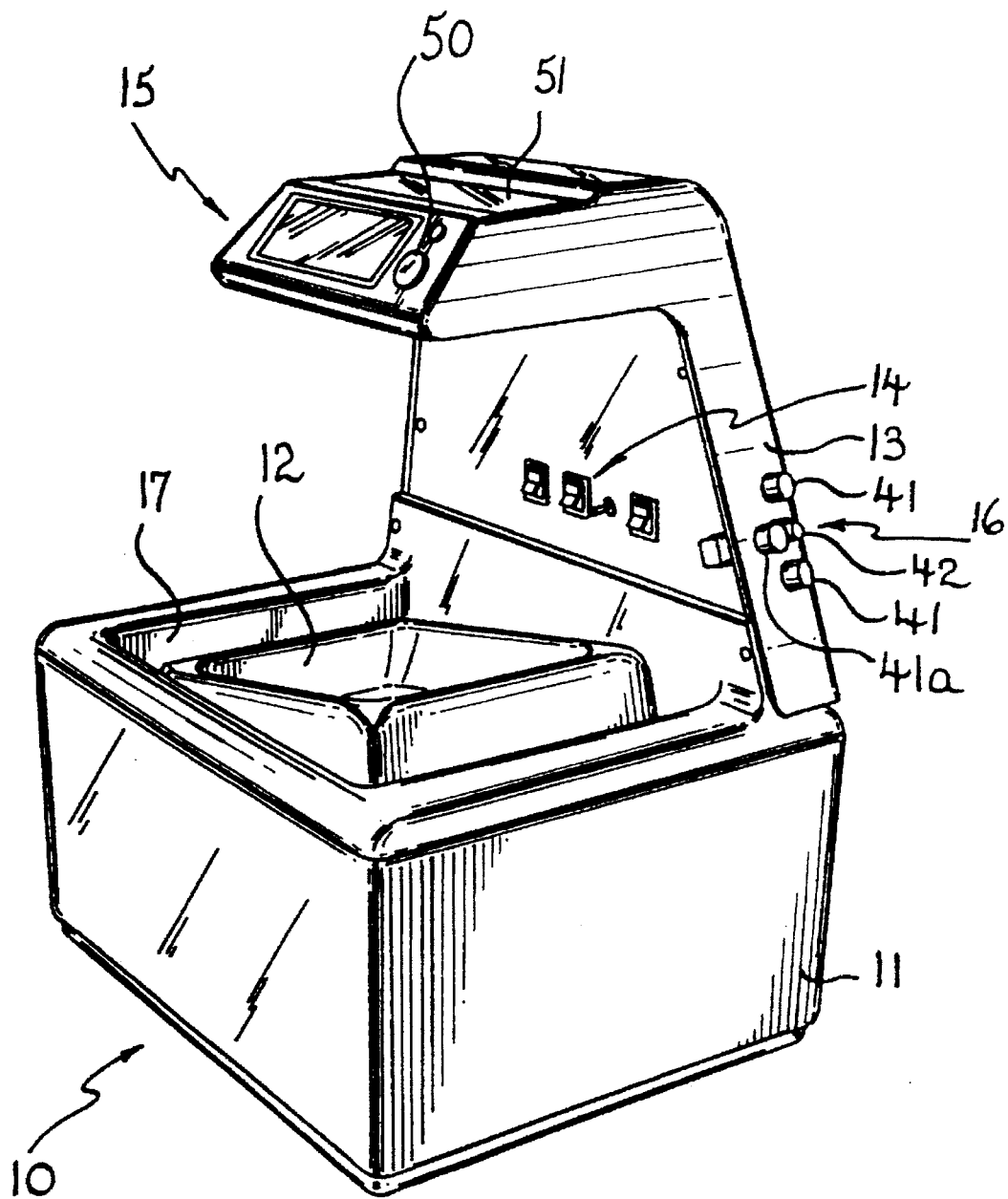
FIG. 1 is an isometric view of a blood collection monitoring apparatus according to the embodiment.
Figure 2:
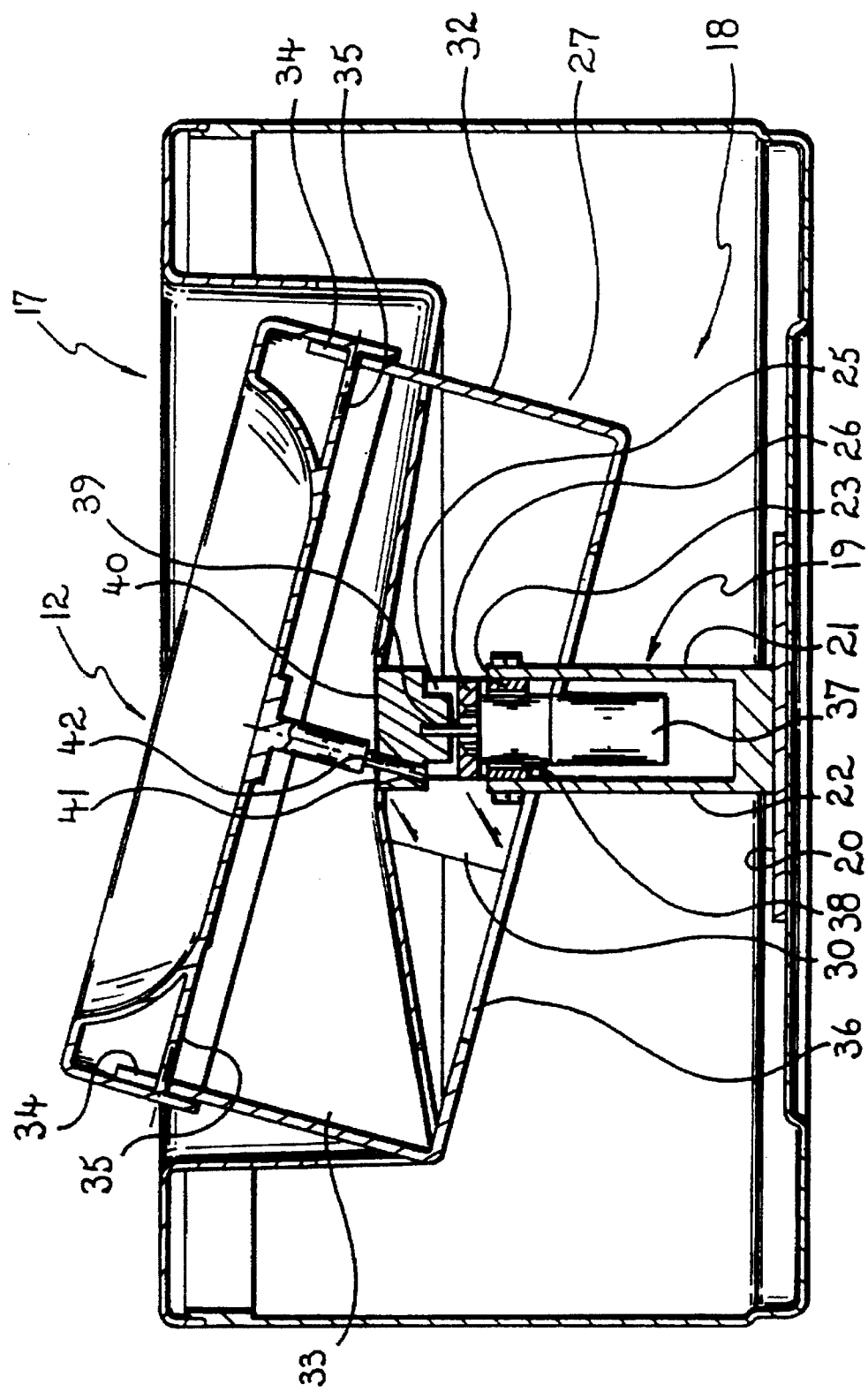
FIG. 2 is a sectional side elevation of the base portion of the embodiment.

The embodiment is directed towards a device which can be used for the collection of blood and monitoring such collection.

According to a further preferred feature of invention the drive means comprises a substantially vertical upright drive shaft having a laterally extending support element, said platform being provided with a downwardly depending member pivotally engagable with the support element whereby rotation of the drive shaft causes said joint pivotal movement of the platform.

According to the preferred feature of the invention the interconnection between the support and the base incorporate a weight sensing and measuring means.

The embodiment comprises a housing 10 having a lower portion 11 which accommodates a support tray 12 and a drive means for causing reciprocation of the tray. The housing further comprises an upper portion 13 which extends upwardly from one side of the base 11 and accommodates an appropriate control switch 14, a display 15, and flow line support 16. Both the lower and upper portion 11 and 13 accommodate the control circuitry for the device.

The lower portion 11 is essentially cubic in configuration and is provided with an open upper face 17. The support tray 12 is configured such that it is received within the upper face 17 and is supported to be able to be caused to pivot about two substantially horizontal perpendicular axes in the open face 17. The tray 12 is formed with an upper face which is recessed in a manner such that it will support a blood collection bag and will prevent substantial movement of the bag on the tray as a result of the cyclic tilting action of the tray.

Figure 3:
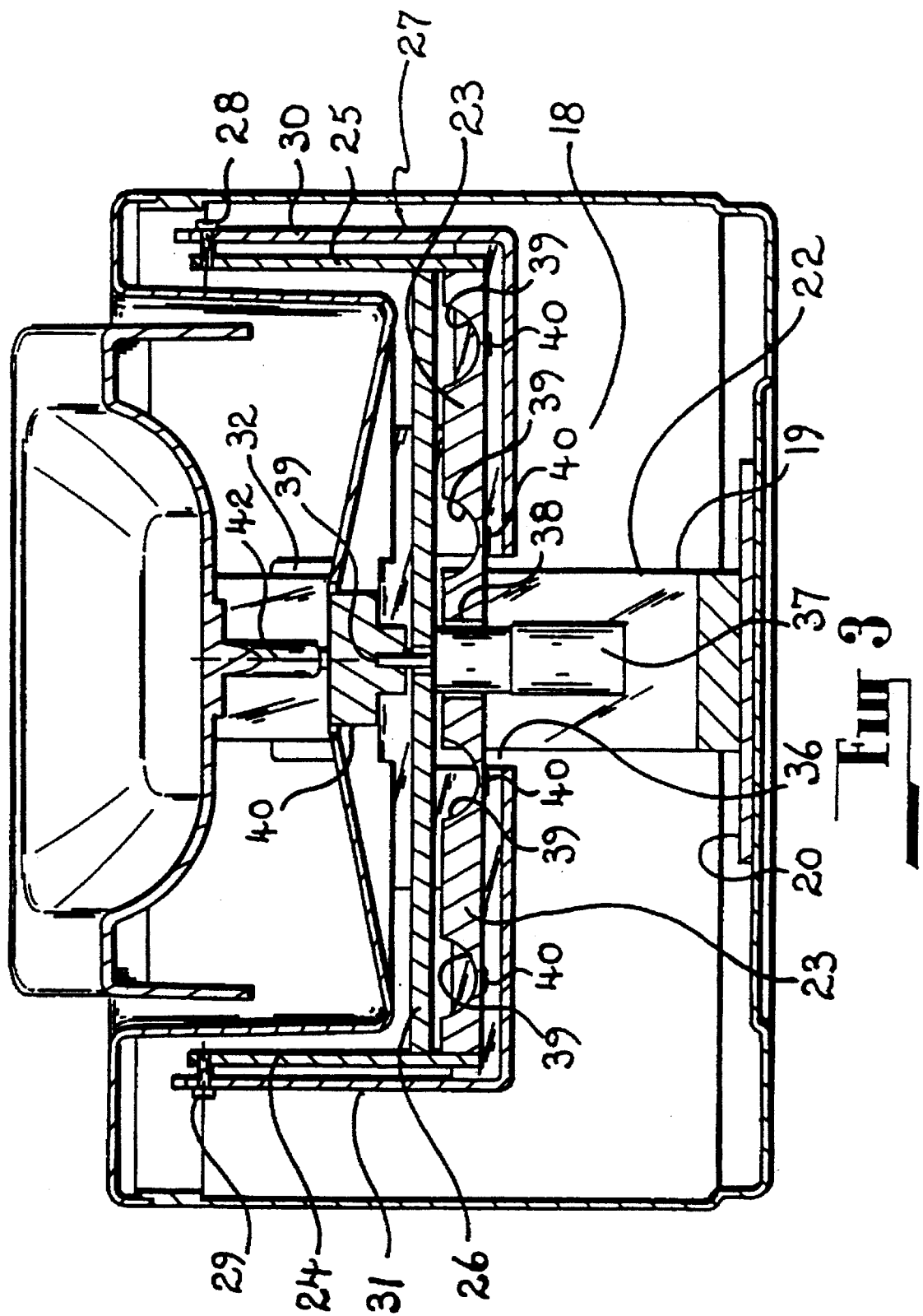
FIG. 3 is a sectional end elevation of the base according to the embodiment.
Figure 4:
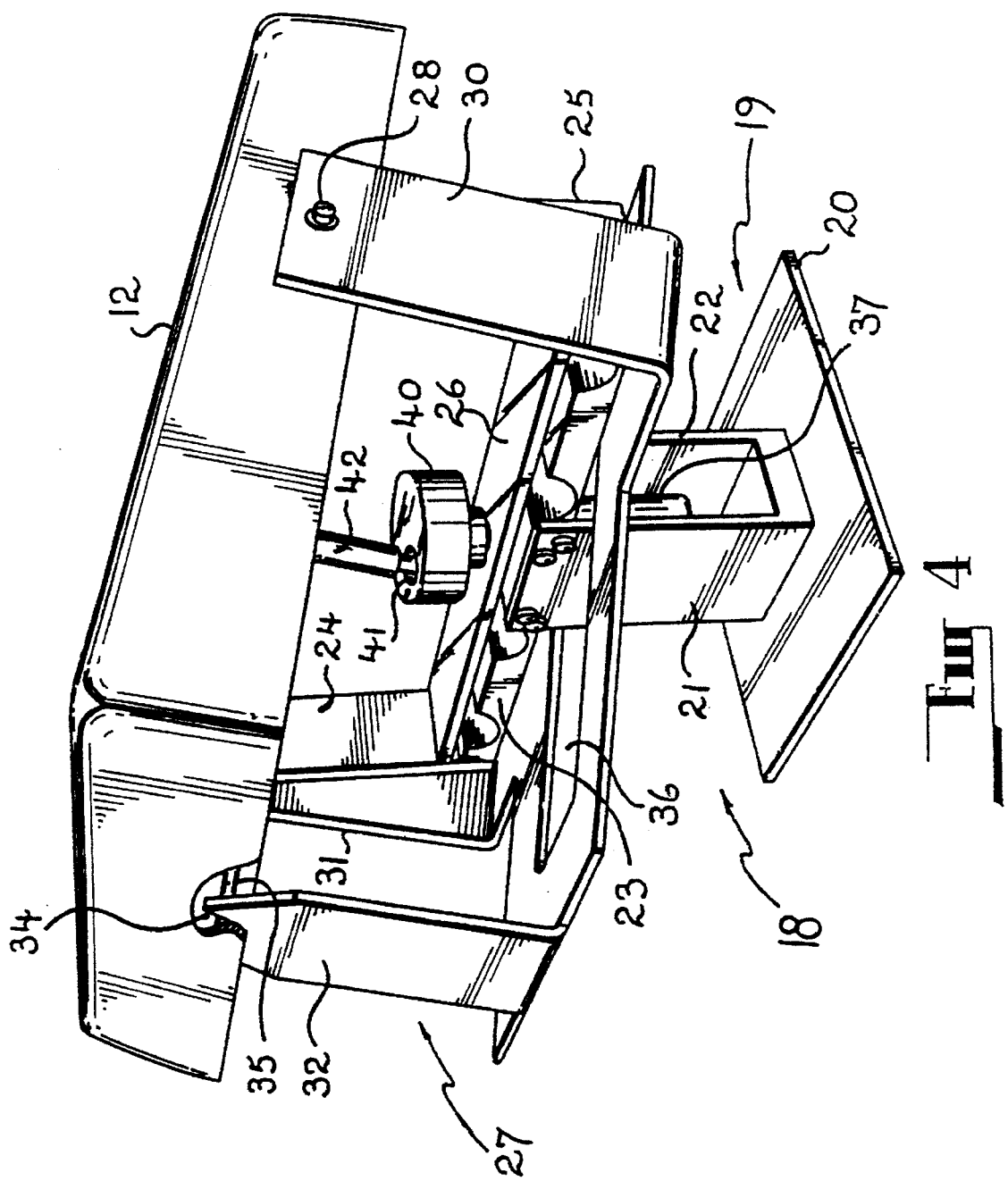
FIG. 4 is an isometric view of the tray support of the embodiment.

The support tray 12 is supported within the base 11 from a support structure 18 (see FIG. 3) which has a base 19 defined by a lower plate 20 which is adapted to be fixed to the bottom wall of the lower portion 11 of the housing. The base has an upstanding pair of parallel webs 21 and 22. The upper ends of the webs 21 and 22 support the central portion of a beam 23 which extends to each side of the space between the webs 21 and 22 and which supports an upright 24 and 25 at each end. The uprights 24 and 25 are further interconnected by a secondary beam 26 which lies parallel to the primary beam 23 and is spaced upwardly therefrom.

The upper end of each of the uprights 24 and 25 pivotally supports a support frame 27 through pivots 28 and 29 where the pivot axis between the pivots 28 and 29 is substantially horizontal.

The support frame 27 is of a generally cruciform configuration where the end of each arm is formed with an upwardly extending portion which provides two pairs of upwardly extending arms. The arms of each pair of arms are opposite each other and the axes interconnecting the pairs of arms are substantially perpendicular. One pair of upwardly extending arms 30 and 31 are pivotally mounted to the uprights 24 and 25 through the pivots 28 and 29 respectively to be pivotally supported from the base element 19 about the axis between the pivots 28 and 29. The other pair of upwardly extending arms 32 and 33 are each formed with a V-shaped recess 34 which each pivotally receive a pivot pin or shaft 35 provided on the underneath the tray 12 towards each end thereof such that the tray is pivotally supported between the second pair of upwardly projecting arms 32 and 33 for pivotable movement about the axis of the shaft 35.

The central portion of the support frame which accommodates the second pair of upwardly extending arms 32 and 33 is formed with a slot shaped aperture 36 which as a width greater than the width of the webs 21 and 22 and which enables the support frame 27 to pivot over the base about the pivots 28 and 29.

The base 19 also supports a drive motor 67 which is supported from the secondary beam 26 to depend downwardly therefrom but which is received within an opening 38 provided in the primary beam 23 such that it does not interfere with and is not supported in any way, by the primary beam 23. The drive motor 67 is provided with an upwardly extending drive shaft 69 which has a wheel 60 mounted to its upper end. The wheel 60 is formed in its upper surface with a socket 61 at a position offset from the central axis of the wheel 60 and the shaft 69. If desired the wheel can be replaced by a crank or like device.

The underneath of the tray 12 is provided with a downwardly depending shaft 62 which is formed at its lower end with a ball-shaped element (not shown) which is pivotally received within the socket 61. The shaft 62 is located centrally on the tray 12. On rotation of the wheel 60 as a result of the activation of the drive motor 67 the free end of the downwardly extending shaft 62 is caused to orbit around the central axis of the shaft and wheel and as a result the tray 12 is caused to pivot about the central axis of the shaft 69 between the second pair of upwardly extending arms 32 and 33 and the axis between the pivots 28 and 29 provided between the uprights 24 and 25 on the base 19. This joint cyclic tilting of the tray 12 about a pair of substantially perpendicular axes provides an action which facilitates the rapid and consistent mixing of blood and anticoagulant within a bag which is supported on the tray 12.

The operation of the drive motor through the control circuit is such that each time the drive motor stops the wheel the tray is at the same position. This is facilitated by the present of the magnet mounted to the wheel 80 (not shown) which is associated with a Hall effect sensor (not shown) provided on the secondary beam 26 to enable the control circuit to always stop the drive motor 67 with the tray in the same position. In use a receptacle is placed on the tray such that the inlet is lowermost. As a result blood entering the receptacle must flow through the anticoagulant accommodated within the receptacle when the tray is stationary.

The mounting and construction of the tray is such that it can be readily lifted out of engagement with the recesses 34 on the arms 32 and 33 of the support frame 27 and out of engagement with the wheel for the tray to be cleaned. When cleaned the tray is readily capable of being re-engaged with the support 27 and the wheel.

It has been found that the repetitive tilting of the tray about two axes, as a result of the construction according to the embodiment, enables the blood, collected during a normal six minute donation period, to be rapidly mixed with the anticoagulant contained within the receiving bag with little segregation of the constituents of the blood, such as accumulation of red blood cells which has been a common difficulty with mechanisms used in the past.

In this regard high concentrations of the anticoagulant has toxic effects on blood while lack of anticoagulant results in the blood results in the initial phases of blood coagulation. If the mixing of the blood with the anticoagulant is slow or not even distributed the blood can remain segregated from the anticoagulant for an extensive period of time. This results in the blood in contact with the anticoagulant being subject to excessive concentrations of anticoagulant and the blood lying in the bottom of the bag which is separated from the anticoagulant commencing the initial coagulation stages.

The primary beam 23 of the base provides the primary support for the tray, its contents and the support frame 27 from the base 19. The primary beam 23 is supported symmetrically from the webs 21 and 22 and also symmetrically supports the tray 12 and its contents. The beam is formed with a set of four symmetrically located transverse grooves 39 and each groove is associated with a strain gauge 40. The strain gauges are interconnected to an electrical circuit which is able to provide a measure indicative of the weight of the tray and its contents. In addition the control circuitry is able to provide a display representative of the weight of the contents of the bag in the tray and the rate of change of the weight of the contents of the tray. The configuration and construction of the primary beam may take any desirable form to facilitate the symmetrical support and use of four strain gauges to provide a measure representative of weight.

In operation the drive motor 67 is activated intermittently whereby during each rest period the weight as sensed by the strain gauges 40, is measured and the change in weight since the previous rest period is determined.

The support arrangement for the tray according to the embodiment as described above comprises a means whereby the pivotal support for the tray and the drive for causing such pivotal movement of the tray is carried from a common carriage which is in turn supported symmetrically from the base element whereby the nature of the support provided for the carriage enables the weight of the tray, the support carriage and the contents of the tray can be accurately monitored, to ensure accurate monitoring of the contents of the tray 12.

The upper portion 13 of the housing is provided with a flow line support 16 which comprises a set of three upwardly fixed extending spigots 41 and a fourth movable spigot 42. The fixed spigots 41 together form a triangular array of spigots. The movable spigot 42 is capable of moving towards the central spigot 41a. In use a blood flow line is laced between the movable spigot 42 and the three fixed spigots 41. The movable spigot 42 is associated with a latch means which is activated by a solenoid or like device which on activation will cause the movable spigot 42 to move towards the fixed spigots 41 whereby the flow line is clamped to prevent flow of blood through that line.

The control of the flow line support means 16 is effected from the control circuit accommodated within the upper portion 13 of the housing to control the flow of blood to the receptacle carried on the tray 12.

The control circuit incorporates a main control switch 50 to initiate the operation of the device. In addition the control circuit is provided with a micro processor which in association with the display 15 provides a set of instructions to the operator and which controls the flow line support in association with those instructions. The control circuit is further provided with appropriate toggle switches 14 and memory circuitry which enable a value for a predetermined volume of blood which is to be collected to be introduced into the memory of the control circuit such that on that volume having been collected the flow line support will be activated to prevent any further flow of blood to the receptacle. On first use of the device the volume or weight of blood to be collected is stored into the memory. This can be varied from time to time but the memory will retain the figure previously entered until it is subsequently changed.

The control circuit is also able to provide a display of the amount of blood collected by indicated the weight of blood collected or the volume of the blood collected. In providing such the circuit operates on the measure derived from the weight sensing circuit to provide a measure of the volume. If desired a suitable switch may be provided with the display to be able to change the display from indicating weight to indicate volume during operation of the device.

The display provides a multiple of displays. On form of display provides an accurate digital display of the volume and/or weight of blood in the collection bag and the time elapsed since the collection of blood commenced. The other form of display comprises an array of lights which are activated sequentially whereby at the commencement of collection no lights are activated and at the termination of collection when the predetermined volume of blood has been collected (irrespective of that amount) all of the lights are lit. As a result the array of lights enable a ready determination to be made of the percentage of the amount to be collected which has actually been received in the collection bag. The display can also provide a periodic audio signal indicative of the percentage of the collection that has been received. This may comprise a variable signal which varies in pitch and frequency throughout the collection period.

At the commencement of the use of the apparatus it is switched on and the user is instructed by the display to locate a collection bag on the tray. Only after a collection bag is located on the tray 12 will be apparatus proceed to the next step at which the display is set to indicate zero in relation to both the weight and/or volume of blood in the collection bag. The sensing of the presence of a collection bag in the tray may be effected by sensing the increased weight of the tray due to the collection bag or by means of a light sensitive cell located on the tray. The flow line to the tray is then installed in the flow line support 16 and is connected to a donor. When the receptacle and flow line are in position, blood begins to flow to the receptacle and on an initial quantity of blood being received (e.g. 20 grams) the control circuit activates the drive motor 67 to cause the cyclic tilting of the tray 12 about its pivot axes. Such activation of the motor is intermittent and is for a period of several rotations of the wheel. During each rest phase the weight of the tray and the receptacle is measured. The control circuit then compares the weight currently being measured with the weight previously measured and provides an indication at the display of the current weight of the contents of the tray.

If desired the display can also provide an indication of the flow rate which is derived from the change in weight of the contents of the tray between the current measurement and the previous measurement. In the event of the flow rate not being within a satisfactory range a further display is provided and the display is associated with a suitable audible alarm to draw the attention of the operator to the low flow rate in order that the matter can be rectified. After intervention by the operator the operator may press the main control switch 50 again whereon the control circuit will enable the display to continue as if the interruption had not occurred.

In addition, the control circuit is such that it will not accept any spurious indicators of mass or volume of the contents of the receptacle which is contrary to the expected flow rate from a donor. Such a circumstance can arise when an operator taps or touches the receptacle which results in an excessive weight being measured by the control circuit and where the weight measured is not representative of the actual weight of the contents of the tray. This rapid weight increase would be beyond that which one would normally expect from a blood donor. The microprocessor is programmed not to accept any measurements which are beyond the normal flow rates expected of a donor and which are not representative of the actual flow rate to the bag. Therefore the control circuit ignores any spurious weight indicators that may result from the receptacle being inadvertently knocked or tapped, and will not shut off the blood flow in the event of such an incident.

The upper portion of the housing is also provided with a set of photovoltaic cells 51 which are associated with a set of electrolytic storage batteries and a charging circuit. These enable the device to be portable and capable of being independent of a mains power supply.

The control circuit also includes a Calibration programme whereby the weighing sensor may be calibrated. The programme provides a sequence of instructions on the display. The instructions require the operator to locate a set of standard weights (e.g. 10 g, 20 g, 30 g weights sequentially) on the tray and on location of each weight the circuit calibrates the sensor. This Calibration programme can be initiated at any time the device is not in collection mode.

It should be appreciated that the scope of the present invention need not be limited to the particular scope of the embodiment described above.

I claim:

1. A mixer, comprising: a support element, a first transverse beam extending laterally from opposite sides of the support element, a first pair of pivots provided on the first transverse beam, on opposite sides of the support element and equidistant from the support element, to provide a first pivot axis, a support pivotally supported from the first pivots to be pivotable about the first pivot axis, the support having a pair of second pivots on opposite sides of the first pivot axis to provide a second pivot axis which is perpendicular to the first pivot axis and which is located between the first pivots, a platform pivotally supported from the second pivots to be pivotable about the second pivot axis, a drive motor supported from the first transverse beam, said drive motor having a drive shaft which is coupled to the platform, whereby rotation of the drive shaft causes joint pivotable movement of the platform about the second pivot axis and the support about the first pivot axis, said first transverse beam being deflectable proportionally to the weight of an item on the platform, and measuring means, connected to the first transverse beam, for measuring the degree of deflection of the beam to provide an indication of the weight and/or volume of the item on the platform.

2. The mixer of claim 1, wherein the weight carried by the first pivots is substantially equal.

3. The mixer of claim 2, wherein the drive shaft and the platform are coupled by a laterally extending member provided on the drive shaft and by a downwardly depending member provided on the platform and pivotally engaged with the laterally extending member, whereby rotation of the drive shaft causes said joint pivotable movement of the platform.

4. The mixer of claim 2, wherein the platform is configured to receive a receptacle in the form of a closed bag formed of a flexible material.

5. The mixer of claim 1, wherein the drive shaft and the platform are coupled by a laterally extending member provided on the drive shaft and by a downwardly depending member provided on the platform and pivotally engaged with the laterally extending member, whereby rotation of the drive shaft causes said joint pivotable movement of the platform.

6. The mixer of claim 1, wherein the platform is configured to receive a receptacle in the form of a closed bag formed of a flexible material.

7. The mixer of claim 6, wherein the platform is formed as a tray having upstanding sides.

8. The mixer of claim 1, wherein the platform is adapted to accommodate a blood collection receptacle.

9. The mixer of claim 1, wherein the second pivots are spaced equidistant to each side of the first pivot axis.

10. The mixer of claim 9, wherein the weight carried by the second pivots is substantially equal.

11. The mixer of claim 9, wherein each of said first pivots is provided by an arm extending from the first transverse beam, and said drive motor is supported from a second transverse beam extending between the arms.

12. The mixer of claim 9, wherein the platform is engaged with the second pivots and the drive motor in a manner that allows the platform to be readily disengaged the second pivots and the drive motor by lifting the platform from the second pivots.

13. The mixer of claim 1, wherein each of said first pivots is provided by an arm extending from the first transverse beam, and said drive motor is supported from a second transverse beam extending between the arms.

14. The mixer of claim 13, wherein the first transverse beam is provided with at least one strain gauge to provide said measuring means.

15. The mixer of claim 14, wherein the drive shaft and the platform are coupled by a laterally extending member provided on the drive shaft and by a downwardly depending member provided on the platform and pivotally engaged with the laterally extending member, whereby rotation of the drive shaft causes said joint pivotable movement of the platform.

16. The mixer of claim 13, wherein the platform is engaged with the second pivots and the drive motor in a manner that allows the platform to be readily disengaged the second pivots and the drive motor by lifting the platform from the second pivots.

17. The mixer of claim 13, wherein the platform is configured to receive a receptacle in the form of a closed bag formed of a flexible material.

18. The mixer of claim 1, wherein the platform is engaged with the second pivots and the drive motor in a manner that allows the platform to be readily disengaged the second pivots and the drive motor by lifting the platform from the second pivots.

19. The mixer of claim 18, wherein the drive shaft and the platform are coupled by a laterally extending member provided on the drive shaft and by a downwardly depending member provided on the platform and pivotally engaged with the laterally extending member, whereby rotation of the drive shaft causes said joint pivotable movement of the platform.

20. A mixer, comprising:

a base;

a generally vertical support mounted on the base;

a generally horizontal beam mounted on the support;

a frame pivotally mounted relative to opposite ends of the beam, wherein the frame pivots about a first pivot axis relative to the beam;

a platform pivotally mounted relative to opposite ends of the frame, wherein the platform is sized and configured to support an item, and the platform pivots about a second pivot axis relative to the frame, and the second pivot axis extends generally perpendicular to the first pivot axis;

a drive motor mounted to at least one of the base, the support, and the beam;

a generally vertical drive shaft interconnected between the drive motor and the platform, wherein rotation of the drive shaft causes joint pivotable movement of the platform about the second pivot axis and the frame about the first pivot axis; and a measuring means, connected to the beam, for measuring at least one of the weight and the volume of an item on the platform.

21. The mixer of claim 20, wherein the second pivot axis is disposed equidistant between the opposite ends of the beam.

22. The mixer of claim 20, wherein the first pivot axis is disposed equidistant between the opposite ends of the frame.

23. The mixer of claim 20, wherein the measuring means includes a plurality of generally transverse grooves formed in the beam, and a strain gauge associated with each of the plurality of grooves and connected to the beam.

* * * * *